United States Patent [19]

Heimburger et al.

[11] Patent Number: 5,043,428

[45] Date of Patent: Aug. 27, 1991

[54] PASTEURIZED, ISOAGGLUTININ-FREE FACTOR VIII PREPARATION AND A PROCESS FOR ITS PRODUCTION

[75] Inventors: Norbert Heimburger, Marburg; Wilfried Wormsbächer, Kirchhain-Niederwald; Gerhardt Kumpe, Wetter, all of Fed. Rep. of Germany

[73] Assignee: Behringwerke Aktiengesellschaft, Marburg/Lahn, Fed. Rep. of Germany

[21] Appl. No.: 538,695

[22] Filed: Jun. 18, 1990

Related U.S. Application Data

[63] Continuation of Ser. No. 165,354, Feb. 29, 1988, abandoned, which is a continuation of Ser. No. 770,674, Aug. 29, 1985, abandoned.

[30] Foreign Application Priority Data

Aug. 31, 1984 [DE] Fed. Rep. of Germany ....... 3432083

[51] Int. Cl.$^5$ ..................... C07K 15/14; C07K 15/06; C07K 3/22; C07K 3/28
[52] U.S. Cl. ........................................ 530/383; 514/8; 514/21; 435/70.2; 435/70.3; 435/70.4; 530/830; 530/831
[58] Field of Search ...................... 530/383, 830, 831; 514/8, 4; 425/70.2, 70.3, 70.4

[56] References Cited

U.S. PATENT DOCUMENTS

| | | | |
|---|---|---|---|
| Re. 32,011 | 10/1985 | Zimmerman et al. | 260/112 B |
| 4,093,608 | 6/1978 | Iga et al. | 260/112 B |
| 4,297,344 | 10/1981 | Schwinn et al. | 424/101 |
| 4,302,445 | 11/1981 | Pla et al. | 424/101 |
| 4,348,315 | 9/1982 | Blomback et al. | 260/112 B |
| 4,435,318 | 3/1984 | Pabst et al. | 260/112 B |
| 4,440,679 | 4/1984 | Fernandes et al. | 260/112 B X |
| 4,495,175 | 1/1985 | Chavin et al. | 260/112 B X |
| 4,508,709 | 4/1985 | Amphlett et al. | 424/101 |
| 4,562,072 | 12/1985 | Heimburger et al. | 424/101 |
| 4,578,218 | 3/1986 | Saundry et al. | 260/112 B |
| 4,743,680 | 5/1988 | Mathews et al. | 530/383 |
| 4,758,657 | 7/1988 | Farb et al. | 530/383 |

FOREIGN PATENT DOCUMENTS 883549  11/1961  United Kingdom ................. 424/85

OTHER PUBLICATIONS

Van Creveld et al., Thromb. Diath-Haem-(1961), VI, No. 2/3, 282-286.
Baugh et al., Biochim, Biophys. Acta (1974), 371, 360-367.
Austen, Brit. J. Haemotology, 43 (1979), 669-674.
Tuddenham et al., J. Lab. Clin. Med. 93 (1979), 40-53.
Chem. Abstracts, 101, 60117g, Behringwerke. Apr. 12, 1984.
Proc. Natl. Acad. Sci. U.S.A. 79, 1648-1652 (1982). Fulcher et al.
Proc. Natl. Acad. Sci. U.S.A. 79, 7200-7204 (1982), Fay et al.
British J Haematology, 9 (1963) 236-244. Michael et al.
A. Faure et al., Journal of Chromatography, 257 (1983), pp. 387-391.
Lundblad et al., Thrombosis Research, vol. 1, No. 2 (1972), pp. 197-200. "The Effect of Dextrose on Chromatography of Antihemophilic Factor (Factor VIII)".

*Primary Examiner*—Howard E. Schain
*Attorney, Agent, or Firm*—Finnegan, Henderson, Farabow, Garrett, and Dunner

[57] ABSTRACT

A process for the production of a preparation of blood coagulation factor VIII which makes it possible to obtain a pasteurized product which is virtually free of immunoglobulins, isoagglutinins, fibronectin and coagulable fibrinogen is described.

A product of this type can be used for the treatment of blood coagulation disturbances.

15 Claims, No Drawings

PASTEURIZED, ISOAGGLUTININ-FREE FACTOR VIII PREPARATION AND A PROCESS FOR ITS PRODUCTION

This application is a continuation of application Ser. No. 7/165,354, filed Feb. 29, 1988, now abandoned, which is a continuation of application Ser. No. 770,674, filed Aug. 29, 1985, now abandoned.

The invention relates to a process for the production of a pasteurized and purified preparation of blood coagulation factor VIII. This preparation can be used for the treatment of blood coagulation disturbances.

Blood coagulation is a complex process which takes place via several reaction steps and which involves at least 13 coagulation factors (F) which are identified by roman numerals. The coagulation factors are predominantly proteins and, in particular, proteins equipped with the properties of proteases or accelerators. The only actual substrate is fibrinogen which, in cases of injury, is converted by thrombin into its insoluble form, fibrin, which forms the primary wound closure. If one of the 13 coagulation factors is missing, the formation of thrombin and fibrin does not take place; the consequence is hemorrhage. An instance of this is hemophilia A which is the most widespread disease with a tendency to hemorrhage and which is due to a deficiency of factor VIII. Both hemophilia A and B (F IX deficiency) can only be effectively treated by replacement of the factor which is lacking.

The problem of obtaining F VIII from human plasma in good yield and high purity, as is necessary, in particular, for the self-treatment of patients, still has no optimal solution. This particularly applies to pasteurized F VIII concentrates which have increasingly displaced the conventional commercial product because it has been possible with them to eliminate the risk of transmission of hepatitis.

The isolation of a highly purified F VIII in good yield is made difficult by, in particular, the fact that although F VIII is enriched in the cryoprecipitate, it is associated with fibrinogen and fibronectin, which are two proteins which have relatively high molecular weights and are sparingly soluble and have similar physicochemical properties to F VIII.

A factor VIII concentrate should be as pure as possible, that is to say free of undesired concomitant proteins and, in particular, of immunoglobulins, including isoagglutinins; this is because there are indications that administration of non-specific proteins leads to overstrain of the reticuloendothelial system (RES) and to impairment of the immune defenses manifested by a change in the composition of the lymphocyte population and of the immunoglobulins. The significance of this becomes more evident when connected with the fact that hemophiliacs have to undergo life-long treatment with such F VIII concentrates. This results in the demand for a native, highly purified, pasteurized F VIII concentrate, i.e. a product which rules out transmission of hepatitis viruses and other infectious material and rules out sensitization to isoantigens.

This invention relates to a product of this type which rules out the transmission of hepatitis and is free of isoagglutinins, and to a process for its production.

It has been found that a solution containing F VIII but which is virtually free of factors of the prothrombin complex (F II, VII, IX and X) can be pasteurized in a manner known per se after the addition of stabilizers to protect against thermal inactivation, the heated solution can be treated with an anion exchanger in the pH range 5–6.5, and the adsorbed F VIII can be washed free of concomitant proteins, especially fibrinogen, fibronectin and immunoglobulins, including isoagglutinins, eluted with a concentrated solution of Na, K or Ca salts with a halogen, and obtained by, for example, precipitation from the eluate.

Ecteola-cellulose and an anion exchanger bearing QAE (quaternary aminoethyl) groups have already been used for the purification of F VIII (van Creveld, S. et al., Thromb. Diath. Haem. (1961) VI, No. 2/3, 282 and Baugh, R. et al., Bioch. Biophys. Acta (1974) 371. 360). However, transfer to pilot-plant or manufacturing scale has not been possible. It has merely been possible to use ion exchange chromatography for the final purification of prefractionated material (Fay, Ph. J. et al., Proc. Natl. Acad. Sci. (1982) 79, 7200). Adsorption with high specificity takes place only at a pH around 5.5; however, at this most of the proteins contained in the cryoprecipitate, in particular human fibrinogen, precipitate out, especially on contact with the adsorbent in the column. Moreover, according to the papers quoted, relatively large amounts of adsorbent are necessary. This in turn appears to have had an enormous effect on the yield, which was tiny, apparently owing to non-specific adsorption of F VIII—its physiological task is, after all, to adhere to non-physiological surfaces—to the large amounts of adsorbent. It was also found that the material finally purified on a QAE exchanger rapidly lost activity; for this reason, anion exchangers have not been used for the manufacture of F VIII.

However, it has now been found, surprisingly, that chromatography on basic ion exchangers is perfectly suitable for the manufacture of F VIII preparations. It was surprising that, starting from a pasteurized cryoprecipitate, it is possible to obtain a highly purified F VIII preparation in one step by using anion exchange chromatography.

Thus the invention relates to a process for the production of a factor VIII preparation, in which a solution containing factor VIII is, in the presence of stabilizers, pasteurized and purified, which process comprises the solution being treated with an anion exchanger which is based on carbohydrates, the exchanger being washed, and the F VIII being eluted.

Suitable starting materials are a cryoprecipitate obtained by the method of Pool et al., Nature (1964) 203 312, Cohn fraction I (Minot, G. R. et al. J. Clin. I -est. (1945) 24, 7047, plasma, F VIII:C-containing cell culture medium and side fractions containing F VIII obtained from the latter. However, it is advantageous to use directly cryoprecipitate or Cohn I fraction.

It is possible to use as the stabilizer, for protection against thermal inactivation of F VIII during pasteurization, carbohydrates and amino acids, preferably 35–60 g of sucrose per 100 g of solution and 1–3 mol of glycine per liter of solution and, where appropriate, calcium ions. The method can be that of, for example, German Offenlegungsschrift 2,916,711 or 3,237,512.

Examples of suitable anion exchangers for the adsorption of F VIII are exchangers bearing DEAE, QAE or ecteola groups, specifically those based on, in particular, cellulose, sephadex or sepharose, but DEAE-sepharose is preferred.

In contradistinction to van Creveld and Baugh (see above) these exchangers are in fact suitable for purification of F VIII, but under conditions which have not hitherto been disclosed and are described below.

The adsorption conditions have proved to be vital. This is because it has been found, likewise surprisingly, that in a physiological saline medium, preferably at pH 5.5, F VIII is substantially selectively bound to DEAE-sepharose, while concomitant proteins, such as fibrinogen and fibronectin, remain in the supernatant (batch process) or pass through a column. Finally, it has been found, again surprisingly, that a pasteurized solution of the cryoglobulins can in fact be chromatographed at pH 5.5 in a physiological saline medium, since certain cryoglobulins precipitate under these conditions, especially fibrinogen. The adsorption and, in particular, the specificity with which F VIII is bound to the anion exchangers decrease greatly as neutrality is approached. However, under normal chromatography conditions, DEAE is only loaded when the pH exceeds 7.0. Nevertheless, precipitation does not take place in the process described here, because the carbohydrates which have been present in the cryosolutions since the pasteurization keep the fibrinogen and cig in solution in a slightly acid medium.

Thus an advantage of the process described is that on adsorption of pasteurized cryoglobulin onto the anion exchanger the fibrinogen and fibronectin remain in the supernatant or effluent and can be obtained from them as pasteurized products. An example of a method for fibronectin is in German Offenlegungsschrift 2,848,529.

The chromatography on, for example, DEAE- or QAE-exchangers is carried out in a slightly acid medium (pH 5.5) and on exchangers which have been appropriately equilibrated, for example with 0.1 mol/l Na acetate buffer containing 0.1 mol/l lysine. It is also possible to use this buffer to dilute the pasteurized solution containing F VIII to twice the volume before it is treated with the exchanger in a batch or column process. Batch adsorption, which is preferably used, has the advantage that it is possible to follow the binding of F VIII to the exchanger during adsorption by functional determination of F VIII in the supernatant, and, after the activity has disappeared, it is possible to separate the nonadsorbed factors from the ion exchanger by sedimentation or centrifugation and, immediately thereafter, to start with the washing of the exchanger loaded with F VIII. Whereas the washing is advantageously carried out as a batch process, for example on a suction filter, it is advisable to transfer the exchanger to a column for the solution since elution by column chromatography has the advantage that the F VIII is obtained in a relatively concentrated form—of the order of 50–100 IU F VIII/ml under experimental conditions.

The buffers which are suitable for washing the exchanger which is loaded with F VIII are, in particular, those which, on the one hand, do not dissolve off the F VIII but, on the other hand, are suitable for removal, which is as nearly quantitative as possible, of nonspecific proteins, such as the immunoglobulins, and thus also the isoagglutinins. Surprisingly, an appropriate buffer has proved to be a buffer in which the starting material can be dissolved for the adsorption and which contains 0.1 mol/l Na acetate, 0.1 mol/l lysine and 1 g/l NaCl at pH 5.5. The ion exchanger loaded with F VIII was washed with this buffer until the eluate was free of isoagglutinins. The highly sensitive Coombs test was used for testing, this also indicating incomplete antibodies.

Concentrated salt solutions, for example those containing NaCl, are suitable for the desorption of the F VIII from the anion exchangers.

However, other salts of halogens with Na, K or Ca have proved to be more advantageous: KBr, NaBr and $CaCl_2$. They have the advantage that the F VIII is eluted as a relatively sharp peak with a high activity per unit volume, and this is an important advantage for the precipitation.

The concentrations are in the range 0.05 mol/l up to the saturation limit.

Finally, the yield also depends quite significantly on the rate of elution, which should be of the order of 1–10 $ml/cm^2/h$, preferably 5–7 $ml/cm^2/h$.

The eluate containing F VIII can be concentrated by the customary methods, that is to say by precipitation with neutral salts, such as ammonium sulfate or NaCl, advantageously with NaCl which can be dialyzed out more rapidly than ammonium sulfate and, moreover, need not be removed completely.

The further processing of the precipitate containing F VIII is carried out in such a manner that the residue from the precipitation is dissolved in, for example, a buffer of pH 6.9 which contains Na citrate (0.02 mol/l), NaCl (0.06 mol/l), glycine (20 g/l) and albumin (5 g/l) (dialysis buffer) and is dialyzed to equilibrium against the same buffer without albumin. The dialyzed solution is diluted with the albumin-containing dialysis buffer to an activity of 25 to 30 IU F VIII/ml and, after sterilization by filtration, is dispensed into containers and, where appropriate, freeze-dried. The final product is a white lyophilizate which dissolves in less than one minute, has a F VIII activity of 5–10 IU/mg protein, and is pasteurized and free of isoagglutinins. Compared with products of the state of the art, it has the advantage that it contains no undesired proteins, in particular those which, as isoantigens, might lead to sensitization. The product has not given rise to blood-group incompatibilities. Transmission of viral diseases, in particular the various types of hepatitis, appears to be ruled out. The advantages of the process include the facts that it is relatively straightforward and thus can be transferred without difficulty to an industrial scale and that it comprises few working steps. The small number of working steps is reflected by the good yield, since experience has shown that every purification step is associated with loss of activity to a greater or lesser extent.

Thus the invention also relates to a highly purified, pasteurized factor VIII preparation which is virtually free of immunoglobulins, isoagglutinins, fibronectin and coagulable fibrinogen and which has a specific clotting (C) activity (F VIII:C) of about 100 U/mg protein and a ratio of F VIII:C to F VIII R:Ag (related antigen) of >1.

F VIII can be determined by the following procedure: One part, for example 0.1 ml of partial thromboplastin, for example that prepared by the method of German Offenlegungsschrift 2,316,430, is mixed with one part of F VIII-deficient plasma and one part of diluted normal plasma. This mixture is maintained at 37° C. for 6 minutes. After the addition of one part of a 0.025 molar calcium chloride solution prewarmed to 37° C., the time which elapses between addition of the calcium chloride solution and the appearance of a clot is determined. A calibration curve drawn up using serial dilutions of normal plasma is used for quantitation.

1 international unit (= 1 IU) of F VIII is equivalent to the F VIII activity of 1 ml of normal plasma as a substandard to the 3rd International WHO Standard.

The process for obtaining a pasteurized F VIII preparation which is free of isoagglutinins is illustrated below:

EXAMPLE

1. Starting material 250 g of crude cryoprecipitate were dissolved by heating at 30°–37° C. in 750 ml of an NaCl solution (0.08 mol/l), which contained glycine (0.25 mol/l) and heparin (1.25 USP-U/ml). This resulted in 1,000 ml of a solution with a concentration of 0.06 mol/l NaCl, 0.2 mol/l glycine and about 1 USP-U heparin/ml. The pH of the solution was adjusted with 1N HCl to 6.5.

2. Aluminium hydroxide adsorption 80 ml of a suspension containing 10 g/l aluminium hydroxide (Behringwerke Marburg) were added to 1,000 ml of solution from 1. and the mixture was stirred for 15 minutes (temperature about 30° C.). It was then centrifuged at 3,000×g for 15 min, the residue was discarded, and the supernatant was pasteurized after the addition of stabilizers.

3. Pasteurization

The following stabilizers were added, in this sequence, to 1,000 ml of supernatant from 2:

5 ml of $CaCl_2$ solution, 1 mol/l (5 mmol/l)
1,000 g of sucrose (500 g/kg solution)
150 g of glycine (2 mol in 1 l of solution).

The pH was adjusted with 2N NaOH to 7.3. The volume increased to 1,700 ml owing to the additions. The solution was kept at 60° C. in a water bath for 10 hours.

4. Ion exchanger treatment 1,700 ml of solution from 3. were diluted with 1,700 ml of a solution which contained 0.2 mol/l Na acetate, pH 5.5, and 0.2 mol/l lysine. The pH was adjusted with dilute acetic acid to 5.5, and 70 ml of DEAE-sepharose 6 B Cl, equilibrated with a solution containing Na acetate (0.1 mol/l), pH 5.5, lysine (0.1 mol/l) and NaCl (1 g/l), were added. The mixture was stirred at room temperature for 2–3 hours, and the binding of the F VIII was determined by determination of the activity in the supernatant. When the F VIII activity had decreased from 4 IU to 0.1 IU/ml, the adsorbent was removed by centrifugation.

The supernatant was poured off and the adsorbent was separated from the remainder of the supernatent. Entrapped protein was removed from the sepharose by washing with a solution containing 0.1 mol/l Na acetate, pH 5.5, 0.1 mol/l lysine and 1 g/l NaCl, and it was then transferred as a slurry in the same buffer to a column (dimensions: 10×3 cm).

The exchanger was washed in the column until there was no longer any measurable absorption of light at 280 nm and the isoagglutinin values in the Coombs test were at the detection limit.

5. Elution

The exchanger from 4. was eluted with a solution, of pH 5.5, containing 0.1 mol/l Na acetate, 0.1 mol/l lysine and 0.3 mol/l $CaCl_2$. This resulted in the appearance of a peak measurable at a wavelength of 280 nm. The corresponding fractions were collected, and a volume of 180 ml containing 40 IU F VIII/ml was obtained.

6. Precipitation of F VIII 2.2 mol/l glycine and 150 g/l NaCl were added to 180 ml of eluate from 5., and the mixture was stirred at room temperature for 30 min.

The precipitation was recognizable by a marked opalescence. The precipitate was separated off by centrifugation at 30,000×g in an ultracentrifuge for 30 min and, after the supernatant had been poured off, it was kept at 4° C. overnight.

7. Working up

The precipitate from 6. was taken up in 145 ml of buffer, of pH 7.0, which contained 0.02 mol/l tri-Na citrate, 0.06 mol/l NaCl, 10 g/l glycine and 5 g/l human albumin (dissolving buffer). The activity determined in the solution was 40 IU F VIII:C/ml. It was dialyzed against the abovementioned buffer containing no albumin, at room temperature for 3 hours, and the dialyzate was warmed to 30° C. and centrifuged at 30,000×g and 25° C. for 30 minutes. After determination of F VIII, which showed 36 IU/ml, the solution was adjusted to 30 IU/ml with dissolving buffer, and the solution was warmed to 37° C. and sterilized by filtration through a membrane filter.

It was dispensed into vials, frozen and freeze-dried.

We claim:

1. A process for the production of a Factor VIII preparation comprising the steps of:

dissolving at least one of a cryoprecipitate Factor VIII, a plasma, a culture medium from cells synthesizing Factor VIII and Cohn fraction I with the addition of a carbohydrate;

pasteurizing said solution containing Factor VIII;

treating this solution after dilution at a pH of about 5.5 with a carbohydrate anion exchanger effective to bind Factor VIII without retaining fibronectin' and fibrinogen;

washing the exchanger; and eluting the Factor VIII with a solution of calcium ions.

2. A process as claimed in claim 1, wherein Factor VIII is eluted with a solution of $CaCl_2$.

3. The process as claimed in claim 1, wherein the solution containing Factor VIII is a solution of cryoprecipitate which had been treated with aluminium hydroxide or other absorbents to eliminate clotting factors other than F VIII.

4. The process as claimed in claim 1, wherein the solution containing factor VIII is plasma, Cohn fraction I or culture medium from cells synthesizing F VIII.

5. The process as claimed in claim 1, wherein the eluate from the anion exchanger is pasteurized after the addition of amino acids, carbohydrates and calcium.

6. The process as claimed in claim 1, wherein DEAE, QAE, amine resins or ecteola derivatives of cellulose, ®Sephadex or ®Sepharose are used as anion exchangers.

7. The process as claimed in claim 1, wherein the absorbent is washed with a dilute buffered salt solution.

8. The process as claimed in claim 1, wherein elution is carried out with a concentrated buffered aqueous solution of a salt of sodium, potassium or calcium with halogens.

9. The process as claimed in claim 1, wherein said cryoprecipitate Factor VIII, plasma, culture medium from cells synthesizing Factor VIII or Cohn fraction I is additionally dissolved in an amino acid.

10. The process as claimed in claim 1, wherein said carbohydrate is sucrose.

11. The process as claimed in claim 10, wherein said sucrose is present in an amount ranging from about 35 to about 60 grams per 100 grams of solution.

12. The process as claimed in claim 9, wherein said amino acid is glycine.

13. The process as claimed in claim 12, wherein said glycine is present in an amount ranging from about 1 to about 3 moles per liter of solution.

14. The process as claimed in claim 1, wherein said cryoprecipitate Factor VIII, plasma, culture medium from cells synthesizing Factor VIII or Cohn fraction I is additionally dissolved in calcium ions.

15. The process as claimed in claim 14, wherein said calcium ions are present in an amount ranging from about 1 to about 20 mmol/l.

* * * * *

UNITED STATES PATENT AND TRADEMARK OFFICE
CERTIFICATE OF CORRECTION

PATENT NO. : 5,043,428

DATED : August 27, 1991

INVENTOR(S) : Norbert Heimburger et al.

It is certified that error appears in the above-identified patent and that said Letters Patent is hereby corrected as shown below:

On the Title page, after Abstract, "15" should be --14--.

Delete Claim 4 in its entirety.

Signed and Sealed this

Twenty-seventh Day of April, 1993

Attest:

MICHAEL K. KIRK

*Attesting Officer*   Acting Commissioner of Patents and Trademarks

United States Patent [19]

Heimburger et al.

[11] Patent Number: 5,043,428

[45] Date of Patent: Aug. 27, 1991

[54] PASTEURIZED, ISOAGGLUTININ-FREE FACTOR VIII PREPARATION AND A PROCESS FOR ITS PRODUCTION

[75] Inventors: Norbert Heimburger, Marburg; Wilfried Wormsbächer, Kirchhain-Niederwald; Gerhardt Kumpe, Wetter, all of Fed. Rep. of Germany

[73] Assignee: Behringwerke Aktiengesellschaft, Marburg/Lahn, Fed. Rep. of Germany

[21] Appl. No.: 538,695

[22] Filed: Jun. 18, 1990

Related U.S. Application Data

[63] Continuation of Ser. No. 165,354, Feb. 29, 1988, abandoned, which is a continuation of Ser. No. 770,674, Aug. 29, 1985, abandoned.

[30] Foreign Application Priority Data

Aug. 31, 1984 [DE] Fed. Rep. of Germany ....... 3432083

[51] Int. Cl.⁵ .................... C07K 15/14; C07K 15/06; C07K 3/22; C07K 3/28
[52] U.S. Cl. ......................... 530/383; 514/8; 514/21; 435/70.2; 435/70.3; 435/70.4; 530/830; 530/831
[58] Field of Search .............. 530/383, 830, 831; 514/8, 4; 425/70.2, 70.3, 70.4

[56] References Cited

U.S. PATENT DOCUMENTS

| | | | |
|---|---|---|---|
| Re. 32,011 | 10/1985 | Zimmerman et al. | 260/112 B |
| 4,093,608 | 6/1978 | Iga et al. | 260/112 B |
| 4,297,344 | 10/1981 | Schwinn et al. | 424/101 |
| 4,302,445 | 11/1981 | Pla et al. | 424/101 |
| 4,348,315 | 9/1982 | Blomback et al. | 260/112 B |
| 4,435,318 | 3/1984 | Pabst et al. | 260/112 B |
| 4,440,679 | 4/1984 | Fernandes et al. | 260/112 B X |
| 4,495,175 | 1/1985 | Chavin et al. | 260/112 B X |
| 4,508,709 | 4/1985 | Amphlett et al. | 424/101 |
| 4,562,072 | 12/1985 | Heimburger et al. | 424/101 |
| 4,578,218 | 3/1986 | Saundry et al. | 260/112 B |
| 4,743,680 | 5/1988 | Mathews et al. | 530/383 |
| 4,758,657 | 7/1988 | Farb et al. | 530/383 |

FOREIGN PATENT DOCUMENTS 883549 11/1961 United Kingdom ............... 424/85

OTHER PUBLICATIONS

Van Creveld et al., Thromb. Diath-Haem-(1961), VI. No. 2/3, 282-286.
Baugh et al., Biochim. Biophys. Acta (1974), 371, 360-367.
Austen, Brit. J. Haemotology, 43 (1979), 669-674.
Tuddenham et al., J. Lab. Clin. Med. 93 (1979), 40-53.
Chem. Abstracts, 101, 60117g, Behringwerke, Apr. 12, 1984.
Proc. Natl. Acad. Sci. U.S.A. 79, 1648-1652 (1982), Fulcher et al.
Proc. Natl. Acad. Sci. U.S.A. 79, 7200-7204 (1982), Fay et al.
British J Haematology, 9 (1963) 236-244, Michael et al.
A. Faure et al., Journal of Chromatography, 257 (1983), pp. 387-391.
Lundblad et al., Thrombosis Research, vol. 1, No. 2 (1972), pp. 197-200. "The Effect of Dextrose on Chromatography of Antihemophilic Factor (Factor VIII)".

*Primary Examiner*—Howard E. Schain
*Attorney, Agent, or Firm*—Finnegan, Henderson, Farabow, Garrett, and Dunner

[57] ABSTRACT

A process for the production of a preparation of blood coagulation factor VIII which makes it possible to obtain a pasteurized product which is virtually free of immunoglobulins, isoagglutinins, fibronectin and coagulable fibrinogen is described.

A product of this type can be used for the treatment of blood coagulation disturbances.

14 Claims, No Drawings